United States Patent
Allaway et al.

(10) Patent No.: US 11,672,263 B2
(45) Date of Patent: Jun. 13, 2023

(54) FOOD PRODUCT FOR REDUCING MUSCLE BREAKDOWN AND METHODS THEREOF

(71) Applicant: MARS, INCORPORATED, McLean, VA (US)

(72) Inventors: David Allaway, Leicestershire (GB); Adrian Hewson-Hughes, Villers Bretonneux (FR)

(73) Assignee: MARS, INCORPORATED, McLean, VA (US)

( * ) Notice: Subject to any disclaimer, the term of this patent is extended or adjusted under 35 U.S.C. 154(b) by 145 days.

(21) Appl. No.: 17/248,467

(22) Filed: Jan. 26, 2021

(65) Prior Publication Data

US 2021/0186055 A1 Jun. 24, 2021

Related U.S. Application Data

(63) Continuation of application No. 16/062,561, filed as application No. PCT/IB2016/057782 on Dec. 19, 2016, now abandoned.

(30) Foreign Application Priority Data

Dec. 17, 2015 (GB) ..................................... 1522304

(51) Int. Cl.
*A23K 20/147* (2016.01)
*A23K 20/158* (2016.01)
(Continued)

(52) U.S. Cl.
CPC .......... *A23K 20/147* (2016.05); *A23K 20/158* (2016.05); *A23K 50/40* (2016.05);
(Continued)

(58) Field of Classification Search
None
See application file for complete search history.

(56) References Cited

U.S. PATENT DOCUMENTS 2,827,452 A    3/1958    Hermann et al.
3,615,675 A    10/1971    Wisdom
(Continued)

FOREIGN PATENT DOCUMENTS

CN    1251021 C    4/2006
CN    101128109 A    2/2008
(Continued)

OTHER PUBLICATIONS

Sugawara, T., et al., Measurement of the Rate of Myofibrillar Protein Degradation Using the Arteriovenous Difference in Plasma 3-Methylhistidine Concentration of Rats, J. Nutr. Sci. Vitaminol., 55 (2009) pp. 381-384. (Year: 2009).*

(Continued)

*Primary Examiner* — Dominic Lazaro
(74) *Attorney, Agent, or Firm* — Baker Botts L.L.P.

(57) ABSTRACT

The present invention relates to methods of determining the levels of 3-methylhistidine before and after a meal in a companion animal, wherein the meal is a pet foodstuff having a particular protein to fat ratio, which is useful in decreasing the levels of 3-methydlhistidine post-prandially and having the beneficial effects as described herein. The pet foodstuff comprises a ratio of protein to fat of 1:0.27 to 1:0.63 on a gram:gram as fed or dry matter basis. The pet foodstuff described is fed to a companion animal for use in reducing and/or preventing sarcopenia. The present invention also relates to methods of feeding the pet foodstuff described and/or dietary regimes to provide the companion animal with the benefit of reducing and/or preventing sarcopenia.

9 Claims, 1 Drawing Sheet

(51) Int. Cl.
*A23K 50/42* (2016.01)
*A23K 50/48* (2016.01)
*A23K 50/40* (2016.01)

(52) U.S. Cl.
CPC .............. *A23K 50/42* (2016.05); *A23K 50/48* (2016.05); *A23V 2002/00* (2013.01); *A23V 2200/316* (2013.01)

(56) References Cited

U.S. PATENT DOCUMENTS

| | | | |
|---|---|---|---|
| 3,653,908 A | 4/1972 | Buck | |
| 3,764,715 A | 10/1973 | Henthorn | |
| 3,882,257 A | 5/1975 | Cagle | |
| 3,916,029 A | 10/1975 | Hildebolt | |
| 3,922,353 A | 11/1975 | Bernotavicz | |
| 3,930,031 A | 12/1975 | Kealy | |
| 4,006,266 A | 2/1977 | Bone et al. | |
| 4,032,665 A | 6/1977 | Miller | |
| 4,088,796 A | 5/1978 | Persson | |
| 4,104,407 A | 8/1978 | Stringer | |
| 4,145,447 A | 3/1979 | Fisher | |
| 4,190,679 A | 2/1980 | Coffee | |
| 4,211,797 A | 7/1980 | Cante et al. | |
| 4,229,485 A | 10/1980 | Brown et al. | |
| 4,260,635 A | 4/1981 | Fisher | |
| 4,366,175 A | 12/1982 | Brown | |
| 4,508,741 A | 4/1985 | Corbett et al. | |
| 4,596,714 A | 6/1986 | Brabbs | |
| 4,689,238 A | 8/1987 | Hitchner | |
| 4,702,924 A | 10/1987 | Owens et al. | |
| 4,777,058 A | 10/1988 | Chandler | |
| 4,822,626 A | 4/1989 | Spanier | |
| 4,857,333 A | 8/1989 | Harold | |
| 4,888,192 A | 12/1989 | Ramnarine | |
| 4,892,748 A | 1/1990 | Andersen et al. | |
| 4,900,572 A | 2/1990 | Repholz | |
| 5,000,940 A | 3/1991 | Staples | |
| 5,000,973 A | 3/1991 | Scaglione | |
| 5,120,554 A | 6/1992 | Farnsworth | |
| 5,240,720 A | 8/1993 | Axelrod | |
| 5,289,795 A | 3/1994 | Mohilef | |
| 5,312,633 A | 5/1994 | Schwartz | |
| 5,431,927 A | 7/1995 | Hand | |
| 5,532,010 A | 7/1996 | Spanier et al. | |
| 5,650,184 A | 7/1997 | Humphry et al. | |
| 5,681,605 A | 10/1997 | Takemori | |
| 5,695,797 A | 12/1997 | Geromini | |
| 5,750,170 A | 5/1998 | Daouse | |
| 5,780,039 A | 7/1998 | Greenberg et al. | |
| 5,887,749 A | 3/1999 | Schommer | |
| 5,897,893 A | 4/1999 | Mohilef | |
| 5,900,248 A | 5/1999 | Crane | |
| 5,925,390 A | 7/1999 | Kornacki | |
| 5,932,258 A | 8/1999 | Sunvold | |
| 5,965,175 A | 10/1999 | Reinhart | |
| 5,968,569 A | 10/1999 | Cavadini | |
| 6,001,400 A | 12/1999 | Burger | |
| 6,042,873 A | 3/2000 | Lawson | |
| 6,083,520 A | 7/2000 | Toneby | |
| 6,113,970 A | 9/2000 | Rainey et al. | |
| 6,117,477 A | 9/2000 | Paluch | |
| 6,156,355 A | 12/2000 | Shields, Jr. et al. | |
| 6,203,825 B1 | 3/2001 | Hodgkins | |
| 6,355,612 B1 | 3/2002 | Ballevre et al. | |
| 6,383,529 B2 | 5/2002 | Davenport et al. | |
| 6,410,063 B1 | 6/2002 | Jewell | |
| 6,517,877 B2 | 2/2003 | Gannon | |
| 6,576,280 B2 | 6/2003 | Bebiak | |
| 6,630,159 B2 | 10/2003 | Sunvold | |
| 6,669,975 B1 | 12/2003 | Abene | |
| 6,672,252 B2 | 1/2004 | Levin | |
| 6,733,263 B2 | 5/2004 | Pope | |
| 6,827,957 B2 | 12/2004 | Paluch | |
| 6,841,178 B2 | 1/2005 | Cupp et al. | |
| 6,896,924 B2 | 5/2005 | Hernandez | |
| 6,904,870 B2 | 6/2005 | Russell-maynard | |
| 6,926,917 B2 | 8/2005 | Parthasarathy | |
| 6,957,914 B2 | 10/2005 | Arends et al. | |
| 6,977,084 B2 | 12/2005 | Bui et al. | |
| 7,120,588 B2 | 10/2006 | Versch | |
| 7,125,574 B2 | 10/2006 | Cupp | |
| 7,288,275 B2 | 10/2007 | Axelrod et al. | |
| 7,479,294 B2 | 1/2009 | Sokhey et al. | |
| 7,485,330 B2 | 2/2009 | Anderson | |
| 7,731,996 B2 | 6/2010 | Bruce | |
| 8,091,509 B2 | 1/2012 | Perez-Camargo et al. | |
| 8,252,742 B2 | 8/2012 | Yamka | |
| 8,691,792 B2 | 4/2014 | Xu | |
| 2001/0048955 A1 | 12/2001 | Foreman | |
| 2002/0150650 A1 | 10/2002 | Cupp | |
| 2003/0026875 A1 | 2/2003 | Aguilar | |
| 2003/0026876 A1 | 2/2003 | Albuja | |
| 2003/0194423 A1 | 10/2003 | Torney | |
| 2004/0005392 A1 | 1/2004 | Filipi | |
| 2004/0022828 A1 | 2/2004 | Sunvold | |
| 2004/0091572 A1 | 5/2004 | Bruce et al. | |
| 2004/0197462 A1 | 10/2004 | Hall | |
| 2004/0244068 A1 | 12/2004 | Heaton | |
| 2004/0247741 A1 | 12/2004 | Guiller | |
| 2004/0253342 A1 | 12/2004 | Townsend | |
| 2005/0186305 A1 | 1/2005 | Rosenberg | |
| 2005/0042330 A1 | 2/2005 | Laborbe | |
| 2005/0106296 A1 | 5/2005 | Merrill | |
| 2005/0181097 A1 | 8/2005 | Townsend | |
| 2005/0238791 A1 | 10/2005 | Mcmindes | |
| 2005/0271709 A1 | 12/2005 | Dazliel et al. | |
| 2006/0062892 A1 | 3/2006 | Merrick | |
| 2006/0134132 A1 | 6/2006 | Watkins et al. | |
| 2006/0188611 A1 | 8/2006 | Unlu et al. | |
| 2006/0204637 A1 | 9/2006 | Hall | |
| 2006/0228448 A1 | 10/2006 | Boileau et al. | |
| 2007/0031542 A1 | 2/2007 | Chu et al. | |
| 2007/0269562 A1 | 11/2007 | Chukwu | |
| 2008/0038403 A1 | 2/2008 | Bierer | |
| 2008/0089984 A1 | 4/2008 | Bruce | |
| 2008/0248156 A1 | 10/2008 | Boileau et al. | |
| 2009/0104315 A1 | 4/2009 | Friesen et al. | |
| 2009/0111877 A1* | 4/2009 | Yamka | A61P 7/02 435/6.16 |
| 2009/0263542 A1 | 10/2009 | Lin | |
| 2010/0303978 A1* | 12/2010 | Sunvold | A23K 40/30 426/311 |
| 2011/0052752 A1 | 3/2011 | Saxe et al. | |
| 2013/0059028 A1 | 3/2013 | Foy et al. | |
| 2013/0281533 A1 | 10/2013 | Yamka et al. | |
| 2014/0141134 A1 | 5/2014 | Johnson et al. | |
| 2014/0161962 A1 | 6/2014 | Boebel et al. | |
| 2017/0112167 A1 | 4/2017 | Cambou | |
| 2017/0176466 A1 | 6/2017 | Alexander et al. | |
| 2018/0000123 A1 | 1/2018 | Duclos et al. | |
| 2018/0295862 A1 | 10/2018 | Mao et al. | |
| 2018/0368446 A1 | 12/2018 | Allaway et al. | |

FOREIGN PATENT DOCUMENTS

| | | |
|---|---|---|
| CN | 101155518 A | 4/2008 |
| CN | 101627824 A | 1/2010 |
| CN | 102573857 A | 7/2012 |
| CN | 101795577 B | 12/2013 |
| CN | 104837358 A | 8/2015 |
| CN | 106360028 | 2/2017 |
| CN | 104010521 B | 4/2018 |
| DE | 29711410 | 12/1899 |
| DE | 3417196 A1 | 11/1985 |
| EP | 0071331 A3 | 7/1983 |
| EP | 0558774 A1 | 9/1993 |
| EP | 0 567 433 A1 | 10/1993 |
| EP | 0594258 A1 | 4/1994 |
| EP | 0769252 A1 | 4/1997 |
| EP | 1036512 A1 | 9/2000 |
| EP | 2875736 A1 | 5/2015 |
| GB | 1465267 A | 2/1977 |
| GB | 2194125 A | 3/1988 |

(56) References Cited

FOREIGN PATENT DOCUMENTS

| | | |
|---|---|---|
| JP | 1014501 | 12/1899 |
| JP | S62296847 A | 12/1987 |
| JP | 2002238464 A | 8/2002 |
| JP | 2004121022 A | 4/2004 |
| JP | 2006510708 A | 3/2006 |
| JP | 2006511209 A | 4/2006 |
| JP | 2013516188 A | 5/2013 |
| JP | 2015156846 A | 9/2015 |
| NL | 7507482 A | 12/1976 |
| RU | 2251364 C1 | 5/2005 |
| RU | 2 403 011 C2 | 11/2010 |
| RU | 2 63 8 525 C2 | 12/2017 |
| WO | 9217072 A1 | 10/1992 |
| WO | 0010405 A1 | 3/2000 |
| WO | 0051443 B1 | 11/2000 |
| WO | 2007060539 A2 | 5/2007 |
| WO | 2007100251 A1 | 9/2007 |
| WO | 2012047800 A1 | 4/2012 |
| WO | 2014092716 A1 | 6/2014 |
| WO | 2014098193 A1 | 6/2014 |
| WO | 2015048339 A2 | 4/2015 |
| WO | 2016130981 A1 | 8/2016 |
| WO | WO 2016/176466 A1 | 11/2016 |

OTHER PUBLICATIONS

Deng, P., Effects of Dietary Macronutrient Profile and Feeding Frequency on Circulating Metabolites, Postprandial Endocrine Response, and Voluntary Physical Activity of Healthy Adult Cats, doctoral dissertation University of Illinois, Urbana-Champaign, 2013. (Year: 2013).*

Anon, Scientific Opinion on the Safety and Efficacy of the Use of Amino Acids (chemical group 34) when used as Flavourings for all Animal Species, The EFSA Journal, vol. 12, No. 5:3670. 10 pages, May 1, 2014.

AOCS Official Method CD 12B-92. "Oil Stability Index", 1997, pp. 1-5.

AOCS Official Method Cd 8b-90. "Peroxide Value Acetic Acid-Isooctane Method", 1997, 2 pages.

Beauchamp, et al., Flavor Preferences in Cats (*Felis catus* and *Panthera* sp.), Journal of Comparative and Physiological Psychology Apr. 1977, vol. 91, No. 5, 1118-1127.

Bradshaw, Food Selection by the Domestic Cat, an Obligate Carnivore, Compl. Biochem. Physiol., 114A, 3:205-209, Jul. 1996.

Bradshaw, Sensory and Experimental factors in the Design of Foods for Domestic Dogs and Cats, Proceedings of the Nutrition Society (Mar. 1991) 50, 99-106.

Bren, Pet Food: The Lowdown on Labels, US Food and Drug Administration, FDA Consumer Magazine, 6 pgs., May-Jun. 2001.

Brown, Digestibility of Pet Foods, Can. Vet. J., Jun. 1987, 314-315.

Burger, Feeding, Catlopaedia, 49-91, Howell Book House, New York, NY, US, 1997.

De Godoy et al, Alternative Dietary Fiber Sources in Companion Animal Nutrition, Nutrients, vol. 5, No. 8, (Aug. 6, 2013), XP055277289, 3099-3117.

Deng, Effects of Dietary Macronutrient Profile and Feeding Frequency on Circulating Metabolites, Postprandial Endocrine Response, and Voluntary Physical Activity of Healthy Adult Cats, Doctoral Dissertation, 2013, 169 pgs.

Deng, P., Effects of Dietary Macronutrient Profile and Feeding Frequency on Circulating Metabolites, Postprandial Endocrine Response, and Voluntary Physical Activity of Health Adult Cats, Doctoral Dissertation University of Illinois, Urbana-Champaign, 2013, 169 pages.

Duclos, The Benefits of Rotation Feeding, http://urbanpawsmagazine.com/archives/59, 5 pgs, Accessed on Nov. 27, 2015.

Fallis, Switching Dog Food Gradually—Guidelines for Success, http://www.petful.com/food/switching-dog-food-gradually/, Oct. 15, 2012, 3 pgs.

Foster, Dog Foods, How to Switch, www.drsforstersmith.com/pic/article.cfm?aid=99, retrieved from the Internet on Nov. 27, 2015, 3 pgs.

Gorrel, The Role of a Dental Hygiene Chew in Maintaining Periodontal Health in Dogs, J. Vet. Dent., Mar. 1, 1996, 13(1), pp. 31-34.

Hewson-Hughes, Geometric Analysis of Macronutrient Selection in the Adult Domestic Cat, Felis Catus, Journal of Experimental Biology, Mar. 2011, 214:1039-1051.

Hill's—The Global Leader in Pet Nutrition; Canine t/d Small Bites; for the Nutritional Management of Dogs with Dental Disease; www.hillspet.com website Jan. 14, 2005, 2 pages.

Hill's—The Global Leader in Pet Nutrition; Canine t/d; for the Nutritional Management of Dogs with Dental Disease; www.hillspet.com website Jan. 14, 2005, 3 pages.

Hill's Nature Best Mature Cat 7+, www.zooplus.co.uk, Jul. 23, 2014, available from https://web.archive.org/web/20140723113636/http:/www.zooplus.co.uk/shop/cats/dry_cat_food/hills_natures_best/95689, 2 pages.

James Wellbeloved Senior 7+ Cat, www.zooplus.co.uk, Jul. 23, 2014, available from https://web.archive.org/web/20150318214301/http:/www.zooplus.co.uk/shop/cats/dry_cat_food/wellbeloved_catfood/wellbeloved_cat_senior/108759, 3 pages.

Lester, Macronutrient Utilization in Cats Fed Low and High Fat Diets, FASEB Journal, vol. 11, No. 3, Nov. 1997, p. A372, Abstract 2156.

Mallery et al., Factors Contributing to the decision for Euthanasia of Dogs with Congestive Heart Failure, J. Am. Vet. Med. Assoc., Apr. 15, 1999, 214(8), p. 1201-4.

Milk-Bone; Treats made for the dog in your life; www.milkbone.com website; Jan. 25, 2005, 1 page.

Nedergaard et al., Serological Loss Biomarkers: An Overview of Current Concepts and Future Possibilities, J. Cachexia Sarcopenia Muscle, 2013, pp. 1-17, vol. 4.

Nutrient Requirements for Cats, National Academy Press, 1986, pp. 3-9, 37-38, 41-44.

Nutrient Requirements for Dogs, National Academy Press, Mar. 1, 1985, pp. 2-5, 7-9, 12-14, 44-45.

Nyman, Dietary Fiber Content and Composition in Six Cereals at Different Extraction Rates, Cereal Chemistry, vol. 61, No. 1, (Jan. 1, 1984), XP055218753.

Pedigree; Pedigree Dentabone for Large Dogs; Snacks & Treats Nutrition for Adult Dogs; www.pedigree.com website; Jan. 25, 2005, 1 page.

Pedigree; Pedigree Jumbone for Large Dogs; Snacks & Treats Nutrition for Adult Dogs; www.pedigree.com website; Jan. 25, 2005, 1 page.

Peterson, Don't Let Your Senior Cat Become a Skinny Old Kitty, URL: http://feline-nutrition.org/nutrition/dont-let-your-senior-cat-become-a-skinny-old-kitty, Sep. 19, 2015, 6 pgs.

Promotional Material regarding the Macronutrient Profile of the Optimum Brand, Mars Petcare, The Waltham Centre for Pet Nutrition, Waltham On the Wolds, GB, Dec. 20, 2006, 16 pgs.

Purina Busy Bone; Beef Flavor Dog Treat for Large dogs; www.purina.com/BusyBone/large.com website; Aug. 26, 2016, 1 page.

Purina Busy Bone; Beef Flavor Dog Treat for small/medium dogs; www.purina.com/BusyBone/small.com website; Jan. 25, 2005, 2 pages.

Purina Dogwiches TM brand Dog Snack; www.purina.com/Dogwiches/mini.asp website; Jan. 25, 2005, 1 page.

Purina Tux, Tux Senior, www.Nestle.co.nz/tux; Internet Wayback Machine, Dec. 21, 2004, 1 page.

Purina Tux; Tux Adult; www.Nestle.co.nz/tux;, Internet Wayback Machine Dec. 21, 2004, 1 page.

Purina Tux; Tux Country; www.Nestle.co.nz/tux; Internet wayback machine Apr. 18, 2005, 1 page.

Purina Tux; Tux Energy Beef & Liver Flavor (Ltd. Ed.); www.Nestle.co.nz/tux; Internet Wayback Machine, Apr. 18, 2005, 1 page.

Rice, The Dog Handbook, pp. 48-49, published by Barron's Educational Series, Oct. 1, 1999.

Rosmos, Regulation of protein intake in adult dogs, JAVMA, vol. 182(1), pp. 41-43, Jan. 1983.

(56) References Cited

OTHER PUBLICATIONS

Royal Canin Indoor +7 Cat, www.zooplus.co.uk, Jul. 17, 2015, available from https://web.archive.org/web/20150717050009/http://www.zooplus.co.uk/shop/cats/dry_cat_food/royal_canin/royalcanin_health_nutrition/14687, 2 pages.
Royal Canin Sterilised 12+ Cat, www.zooplus.co.uk, Mar. 19, 2015, available from https://web.archive.org/web/20150319103701/http://www.zooplus.co.uk/shop/cats/dry_cat_food/royal_canin/royalcanin_health_nutrition/313853, 2 pages.
Royal Canin Sterilized +7 Cat, www.zooplus.co.uk, Mar. 19, 2015, available from https://web.archive.org/web/20150319105235/http://www.zooplus.co.uk/shop/cats/dry_cat_food/royal_canin/royalcanin_health_nutrition/232447, 2 pages.
Serpell, The Domestic Dog, published by Cambridge University Press, pp. 104-106, Sep. 1995.
Sheffield-Moore et al., Isotopic decay of urinary or plasma 3-methylhistidine as a potential biomarker of pathologic skeletal muscle loss, Journal of Cachexia Sarcopenia Muscle, (Mar. 2014) 5:19-25.
Sugawara et al., Measurement of the rate of Myofibrillar Protein Degradation Using the Arteriovenous Difference in Plasma 3-Methylhistidine Concentration of Rats, J. Nutr. Sci. Vitaminol. 55:381-384, Aug. 2009.
Swern, Bailey's Industrial Oil and Fat Products, John Wiley & Sons, NY, "No Month", 1979, pp. 144-146, vol. 1, 4th edition.
The Waltham Book of Dog and Cat Behavior, Ed., C. Thorne, Pergamon Press, PLC, Oxford England, p. 118, 1992.
Think Treats; New Chew Lotta; www.meatybone.com/pages/dogtreats/meatybone/chewlotta.asp website, Jan. 25, 2005, 1 page.
Thorne, Feeding Behaviour of Cats, Cat World (May 1992), 171:20-21.
Wichert et al., Influence of Different Cellulose Types on Feces Quality of Dogs, American Society for Nutritional Sciences, J. Nutr., vol. 132, Issue 6, Jun. 1, 2002, pp. 1728S-1729S.
Willis et al., Basic Principles of Nutrition and Feeding, BSAVA Manual of Companion Animal Nutrition and Feeding, Apr. 19, 1996, British Small Animal Veterinary Association, Shurdington, Cheltenham, UK, Chapter 1, pp. 10-21.
Willis, Adult Maintenance, BSAVA Manual of Companion Animal Nutrition & Feeding, Chapter 3, British Small Animal Veterinary Association, Shurdington, Cheltenham, UK, Apr. 19, 1996, pp. 44-46.

* cited by examiner

FOOD PRODUCT FOR REDUCING MUSCLE BREAKDOWN AND METHODS THEREOF

CROSS-REFERENCE TO RELATED APPLICATIONS

This application is a continuation application of U.S. Ser. No. 16/062,561, filed on Jun. 14, 2018, which is a 35 U.S.C. § 371 national stage application of International Application No. PCT/IB2016/057782, filed Dec. 19, 2016, which claims priority to GB Patent Application Serial No. 1522304.3, filed on Dec. 17, 2015, the entire contents of each hereby being incorporated by reference herein for any and all purposes.

The present invention relates to methods of determining the levels of 3-methylhistidine before and after a meal in a companion animal, wherein the meal is a pet foodstuff having a particular protein to fat ratio, which is useful in decreasing the levels of 3-methydlhistidine post-prandially and having the beneficial effects as described herein. The pet foodstuff comprises a ratio of protein to fat of 1:0.27 to 1:0.63 on a gram:gram as fed or dry matter basis. The pet foodstuff described is fed to a companion animal for use in reducing and/or preventing sarcopenia. The present invention also relates to methods of feeding the pet foodstuff described and/or dietary regimes to provide the companion animal with the benefit of reducing and/or preventing sarcopenia.

In the normal healthy state there is an ongoing balance between synthesis of new proteins to balance the persistent rate of protein breakdown that occurs in all tissues. In the period following food intake, ingested protein can supply amino acids to serve as precursors for the synthesis of new protein to balance this ongoing breakdown. Anything that disturbs or disrupts this balance could result in increased protein breakdown. In terms of the effects on human and animal health and wellbeing, it is recognized that increased protein breakdown and/or reduced protein synthesis results in loss of skeletal muscle mass (described as sarcopenia) and is thus detrimental to health. Sarcopenia (loss of skeletal muscle mass/strength) is associated with weakness and frailty, impaired immune function, poor quality of life and even death. Additionally, for companion animals the deleterious effects associated with skeletal muscle loss, such as weakness, anorexia, weight loss and perceived poor quality of life are major contributing factors for euthanasia decisions by owners (Mallery et al 1999, J Am Vet Med Assoc. 214: 1201-1204). Therefore, because of the option for euthanasia, loss of skeletal muscle mass and the associated morbidities may play an even more important role in survival for cats and dogs.

In addition to its' functional structural, and mechanical roles, skeletal muscle also plays a central role in whole body metabolism. Skeletal muscle serves as the principal reservoir for amino acids that can maintain protein synthesis in vital tissues and organs particularly during the post-absorptive state and in fasting/starvation. During fasting in humans, amino acids derived from skeletal muscle not only provide a substrate for protein synthesis, but also act as precursors for glucose synthesis via hepatic gluconeogenesis. It has been suggested that in cats, gluconeogenesis is not just a response to fasting, but rather a pathway that is constitutively active in order to provide glucose to essential organs such as the brain in a species that has evolved on a natural diet (small animal prey) that is relatively devoid of carbohydrate. Cats may be prone to sarcopenia because of other known metabolic adaptations of cats such as high protein oxidation rates and increased protein turnover. Therefore, an adequate skeletal muscle mass is essential to supply required amino acids in order to maintain the protein turnover of vital tissues and organs in the post-absorptive state and potentially to provide substrate for gluconeogenesis in both fed and fasted states.

There is therefore a need to maintain healthy locomotor function, appropriate metabolic function and optimal quality of life in companion animals in particular to reduce skeletal muscle breakdown so that skeletal muscle mass is maintained.

3-methylhistidine is a direct measure of actomyosin degradation that is not recycled for intermediary metabolism or protein synthesis and so is often used as a marker of skeletal muscle breakdown (Nedergaard, et al., 2013).

The invention relates to a method comprising the following steps: (a) feeding a companion animal, preferably a cat, a foodstuff comprising a protein to fat ratio of 1:0.27 to 1:0.63 on a gram:gram as fed or dry matter basis, and (b) measuring the level of 3 methyl histidine in a blood sample from the companion animal before and after feeding the foodstuff, wherein a reduction and/or maintenance in 3 methyl histidine levels post-prandially is indicative of a foodstuff for use in reducing and/or preventing sarcopenia in the companion animal.

The companion animal, preferably is a cat, in particular a cat that is of senior age, for example at least above 8 years of age.

The levels of 3-methylhistidine are measured at least once between an hour or immediately before the foodstuff is fed to the companion animal, preferably a cat, and at least once between at least 30 minutes to 5 hours after the foodstuff has been fed to the companion animal, preferably a cat.

The foodstuff may have a protein to fat ratio of about 1:0.33 to 1:0.55 on a gram:gram as fed or dry matter basis. The foodstuff may have a protein to fat ratio of about 1:0.45 on a gram:gram as fed or dry matter basis. The foodstuff may have a protein to fat ratio of about 1:0.37 on a gram:gram as fed or dry matter basis. The foodstuff is preferably a nutritionally balanced pet foodstuff. In particular, the foodstuff has a low caloric density.

The method further comprises a step of formulating a foodstuff comprising a protein to fat ratio of 1:0.27 to 1:0.63 on a gram:gram as fed or dry matter basis prior to feeding the companion animal (i.e. a cat) the foodstuff.

The invention also relates to a dietary regime comprising a first stage pet food stuff and a second stage pet foodstuff, wherein the first stage pet foodstuff comprises a ratio of protein:fat of 1:0.27 to 1:0.63 on a gram:gram as fed or dry matter basis and the foodstuff has a first caloric density and wherein the second stage pet foodstuff comprises a ratio of protein:fat of 1:0.27 to 1:0.63 on a gram:gram as fed or dry matter basis and the foodstuff has a second caloric density for feeding a companion animal, preferably a cat, for use in reducing and/or preventing sarcopenia, wherein first stage pet foodstuff is for feeding to a companion animal, preferably a cat, from the age of 1 to approximately 8 years of age and wherein the second stage pet foodstuff is for feeding to a companion animal, preferably a cat, above 8 years of age and wherein the second caloric density is less than the first caloric density.

The first stage or second stage foodstuff may have a protein to fat ratio of about 1:0.33 to 1:0.55 on a gram:gram as fed or dry matter basis. The foodstuff of the first stage or second stage may have a protein to fat ratio of about 1:0.45 on a gram:gram as fed or dry matter basis. The foodstuff of the first stage or second stage may have a protein to fat ratio of about 1:0.37 on a gram:gram as fed or dry matter basis.

The invention further relates to a kit comprising a first stage pet foodstuff and a second stage pet food stuff, and a package for separately housing the first stage pet foodstuff and the second stage pet foodstuff, wherein the first stage pet foodstuff comprises a ratio of protein:fat of 1:0.27 to 1:0.63 on a gram:gram as fed or dry matter basis and has a first caloric density, and wherein the second stage pet foodstuff comprises a ratio of protein:fat of 1:0.27 to 1:0.63 on a gram:gram as fed or dry matter basis and has a second caloric density, wherein the second caloric density is less than the first caloric density and wherein the first stage pet foodstuff is for feeding to a companion animal, preferably a cat, from the age of 1 to approximately 8 years of age and wherein the second stage pet foodstuff is for feeding to a companion animal, preferably a cat, above 8 years of age, for use in reducing and/or preventing sarcopenia.

The kit may further comprise an insert placed in the second stage pet foodstuff compartment including feeding instructions.

The invention further relates to a kit comprising a pet foodstuff comprising a ratio of protein:fat of 1:0.27 to 1:0.63 on a gram:gram as fed or dry matter basis and having a high caloric density and instructions for feeding the companion animal, preferably a cat, from the age of 1 to approximately 8 years of age (i.e. of senior age) the pet foodstuff.

In some embodiments, the pet foodstuff comprises a ratio of protein:fat of 1:0.27 to 1:0.63 on a gram:gram as fed or dry matter basis and is for use in reducing and/or preventing sarcopenia in a companion animal. Reducing and/or preventing sarcopenia is indicated by a reducing and/or maintaining the levels of 3-methylhistidine in a blood sample of the companion animal.

The companion animal is a cat, preferably the companion animal is of senior age, most preferably a cat of senior age (8 years or above). The foodstuff is preferably a complete and a nutritionally balanced pet foodstuff.

In some embodiments, the invention relates to a method of reducing and/or preventing sarcopenia in a companion animal, wherein the companion animal is fed a pet foodstuff comprising a ratio of protein:fat of 1:0.27 to 1:0.63 on a gram:gram as fed or dry matter basis. Reducing and/or preventing sarcopenia is indicated by a reducing and/or maintaining the levels of 3-methylhistidine in a blood sample of the companion animal.

The companion animal is a cat, preferably the companion animal is of senior age, most preferably a cat of senior age (8 years or above).

The pet foodstuff for use and/or used in the methods described for preventing and/or reducing sarcopenia in companion animals is a complete and a nutritionally balanced pet foodstuff.

The pet foodstuff may further comprise one or more nutrients selected from group (a) and group (b), wherein the nutrients in group (a) are aspartic acid, serine, glutamic acid, glycine, alanine or proline and the nutrients in group (b) are myristic acid, palmitic acid, stearic acid, palmitoleic acid, oleic acid or linolenic acid. Preferably, the pet foodstuff comprises one nutrient from group (a) and one nutrient from group (b) and comprises a ratio of 1:0.006 to 1:4.5 on a gram:gram as fed or dry matter basis or wherein the pet foodstuff comprises two nutrients selected from group (a) and two nutrients selected from group (b) and comprises a ratio of 1:0.014 to 1:3.5 on a gram:gram as fed or dry matter basis or wherein the pet foodstuff comprises three nutrients selected from group (a) and three nutrients selected from group (b) and comprises a ratio of 1:0.025 to 1:2.5 on a gram:gram as fed or dry matter basis.

In some embodiments, the invention relates to a dietary regime for feeding a companion animal for use in reducing and/or preventing sarcopenia, wherein the companion animal is fed a combination of at least two pet foodstuffs, wherein one pet foodstuff is wet or dry and comprises a ratio of protein:fat of 1:0.27 to 1:0.63 on a gram:gram as fed or dry matter basis and the second pet foodstuff is wet or dry and comprises a protein:fat ratio of 1:0.27 to 1:0.63 on a gram:gram as fed or dry matter basis, wherein when combined the companion animal is fed an overall ratio of protein:fat of 1:0.27 to 1:0.63 on a gram:gram as fed or dry matter basis.

The present inventors have discovered that the content and proportions of dietary protein and fat in a meal have an impact on the levels of the metabolite 3-methylhistidine and that stabilization and/or reduction in this biomarker can directly be associated with reducing and/or preventing skeletal muscle breakdown and loss of skeletal muscle mass in the companion animal (i.e. sarcopenia).

In the first aspect, the invention relates to a method of determining the level of 3-methylhistidine before and after a meal in a companion animal, wherein the meal is a pet foodstuff having a particular protein to fat ratio which is useful in reducing the levels of 3-methylhistidine post-prandially and having the beneficial effects as described herein.

The method of the invention comprises the following steps of: (a) feeding a companion animal a foodstuff comprising a protein to fat ratio of 1:0.27 to 1:0.63 on a gram:gram as fed or dry matter basis (i.e. the pet foodstuff as described herein), and (b) measuring the level of 3-methylhistidine in a blood sample from the companion animal before and after feeding the foodstuff, wherein a reduction in 3-methylhistidine post-prandially is indicative of a foodstuff for use in reducing and/or preventing sarcopenia in the companion animal.

The purpose of the method of the invention is to provide a diagnosis that the pet foodstuff is the factor providing the effect of reducing the levels of 3-methylhistyidine in the companion animal and thus such pet foodstuff can be useful in providing the beneficial effects of reducing and/or preventing sarcopenia in the companion animal.

The present invention relates, for all aspects, to any companion animal. In particular, the present invention relates to a companion animal such as a dog or a cat. In particular, the companion animal is a cat.

The pet foodstuff comprises a ratio of protein to fat of 1:0.27 to 1:0.63 on a gram:gram as fed or dry matter basis.

The inventors have surprisingly discovered that feeding a companion animal a pet foodstuff having a protein to fat ratio of 1:0.27 to 1:0.63 on a gram:gram as fed or dry matter basis is beneficial in preventing and/or reducing sarcopenia in companion animals.

Post-translational methylation of histidine residues following peptide bond synthesis within the contractile proteins of muscle (actin and myosin) results in the production of 3-methylhistidine. Intracellular degradation of actin and myosin during muscle proteolysis (breakdown) results in the release of 3-methylhistidine into the blood and excretion of unchanged 3-methylhistidine in urine. As 3-methylhistidine cannot be further catabolized nor recycled for intermediary metabolism or protein synthesis it represents a valid marker of skeletal muscle breakdown.

The present invention demonstrates that there is a reduced fasting level and no post-prandial increase in the plasma levels of the skeletal muscle breakdown biomarker 3-methylhistidine by feeding a companion animal, in particular cats, a pet foodstuff comprising a ratio of protein to fat of 1:0.27 to 1:0.63 on a gram:gram as fed or dry matter basis.

3-methylhistidine is a well-known biomarker which provides a direct measure of muscle breakdown and/or muscle mass in a mammal.

A diet that reduces the extent of muscle breakdown in both the fasted and post-prandial state will help support muscle mass. Maintaining muscle mass has many benefits as muscle has a number of important metabolic as well as locomotor functions. The pet foodstuff as described provides this benefit.

The present invention shows that when a companion animal is fed pet foodstuff comprising a ratio of protein to fat of 1:0.27 to 1:0.63 on a gram:gram as fed or dry matter basis, as described in the present invention, the post-prandial levels of 3-methylhistidine are reduced and therefore stabilized. This reduction in 3-methylhistidine biomarker is indicative that the pet foodstuff as described provides the companion animal with the benefit to reduce their skeletal muscle breakdown and/or prevent loss of skeletal muscle mass in order to maintain healthy locomotor function, appropriate metabolic function and optimal quality of life.

The benefits of reducing skeletal muscle breakdown are that normal skeletal muscle mass can be maintained for longer in the lifespan of the animal contributing to the avoidance of weakness, frailty and reduced activity commonly associated with aging in companion animals. Preventing/reducing skeletal muscle breakdown is also beneficial because an adequate skeletal muscle mass is essential to supply required amino acids in order to maintain the protein turnover of vital tissues and organs in the post-absorptive state and potentially to provide substrate for gluconeogenesis in both fed and fasted states.

The pet foodstuff can be fed to a companion animal of any age. In particular, the pet foodstuff can be fed to a senior companion animal. A dog or a cat is considered to be senior when the animal is aged above 8 years. Preferably, the present invention is fed to a senior cat.

Sarcopenia (loss of muscle mass/strength) is common in ageing in companion animals, in particular cats are prone to suffering from sarcopenia.

The present invention can therefore be used to prevent sarcopenia in the companion animal and/or reduce the effects of sarcopenia in a companion animal, in particular of senior age.

The pet foodstuff describe herein is for use in preventing and/or reducing sarcopenia, in particular reducing muscle breakdown in a companion animal.

The pet foodstuff can be fed to a companion animal of any age and at any stage of the companion animal's life. In particular, the pet foodstuff described herein is fed to a companion animal when the animal reaches 5 years and/or senior age of above 8 years old, for example the companion animal can be fed any foodstuff until they reach 5 years of age and then switched to the pet foodstuff described herein to reduce the effects of sarcopenia at later stages of the companion's life.

The pet foodstuff described herein may comprise a ratio of protein to fat on a gram:gram as fed or dry matter basis that may range from 1:0.27 to 1:0.63, 1:0.28 to 1:0.62, 1:0.29 to 1:0.61, 1:0.30 to 1:0.60, 1:0.31 to 1:0.59, 1:0.32 to 1:0.58, 1:0.33 to 1:0.57, 1:0.34 to 1:0.56, 1:0.35 to 1:0.55, 1:0.36 to 1:0.54, 1:0.37 to 1:0.53, 1:0.38 to 1:0.52, 1:0.39 to 1:0.51, 1:0.40 to 1:0.50, 1:0.41 to 1:0.49, 1:0.42 to 1:0.48, 1:0.43 to 1:0.47, 1:0.44 to 1:0.46, and/or combinations thereof. The pet foodstuff may preferably comprise a protein to fat ratio ranging from 1:0.33 to 1:0.55 on a gram:gram as fed or a dry matter basis. The pet foodstuff may comprise a protein to fat ratio that can be selected from 1:0.27, 1:0.28, 1:0.29, 1:0.30, 1:0.31, 1:0.32, 1:0.33, 1:0.34, 1:0.35, 1:0.36, 1:0.37, 1:0.38, 1:0.39, 1:0.40, 1:0.41, 1:0.42, 1:0.43, 1:0.44, 1:0.45, 1:0.46, 1:0.47, 1:0.48, 1:0.49, 1:0.50, 1:0.51, 1:0.52, 1:0.53, 1:0.54, 1:0.55, 1:0.56, 1:0.57, 1:0.58, 1:0.59, 1:0.60, 1:0.61, 1:0.62, or 1:0.63. The pet foodstuff preferably has a protein to fat ratio of about and/or approximately 1:0.45 on a gram:gram as fed or dry matter basis, most preferably the foodstuff has a protein to fat ratio of about and/or approximately 1:0.37 on a gram:gram as fed or dry matter basis.

The pet foodstuff as described herein can consist of a protein to fat ratio of about 1:0.33 to 1:0.55 on a gram:gram as fed or dry matter basis.

The pet foodstuff as described herein can preferably consist of a protein to fat ratio of about 1:0.45 on a gram:gram as fed or dry matter basis or most preferably of a protein to fat ratio of about 1:0.37 on a gram:gram as fed or dry matter basis.

The pet foodstuff can be a complete and nutritionally balanced pet food product.

The foodstuff can be any type which is consumed by the companion animal, such as dry product, semi moist product, wet food product or a liquid and includes any food supplement, snack or treat. This includes, standard food products including liquids, as well as pet food snacks (for example, snack bars, pet chew, crunchy treat, cereal bars, snacks, biscuits and sweet products).

Preferably, the pet foodstuff may be in the form of a dry foodstuff or wet foodstuff. The foodstuff of the first aspect of the invention is, in particular, a nutritionally balanced food product and/or food supplement, for example a pet product and/or pet supplement.

The foodstuff is preferably a pet product. Such a product is preferably sold as a product for feeding/administering to a companion animal, in particular a cat or dog.

The content of protein and/or fat in the pet foodstuff can be any measure and/or weight percentage of the pet foodstuff desired, provided that the final ratio of protein to fat is of 1:0.27 to 1:0.63 gram:gram as fed basis or dry matter basis.

A typical dry pet foodstuff contains about 10-40% crude protein and about 5-40% fat, the remainder being carbohydrate, including dietary fibre and ash. A typical wet or moist product contains (on a dry matter basis) about 40% fat, 50% protein and the remainder being fibre and ash. The foodstuff may be a dry product (with approximately 5 to approximately 15% moisture), a semi-moist product (with approximately 15 to approximately 70% moisture) or a wet product (with approximately 70 to approximately 90% moisture).

As described above, the content of protein and/or fat in the pet foodstuff can be any measure and/or weight percentage of the pet foodstuff desired, provided that the final ratio of protein to fat is of 1:0.27 to 1:0.63 as fed basis or dry matter basis. For example, a wet pet foodstuff may comprise a ratio of protein to fat on a gram:gram as fed ranging from 1:0.27 to 1:0.63, wherein the content of protein is 10 g/100 g as fed basis then the content of fat can be 2.7 g/100 g to 6.3 g/100 as fed basis, most preferably about 4.5 g/100 g as fed basis. For example, the pet foodstuff may be a dry pet foodstuff comprising a ratio of protein to fat on a gram:gram as fed or dry matter basis ranging from 1:0.27 to 1:0.63, wherein the content of protein is 32 g/100 g on an as fed basis then the content of fat can be 8.6 g/100 g to 20.2 g/100 g on an as fed basis, most preferably about 14.4 g/100 g as fed basis.

The foodstuff is preferably a cooked product. It may incorporate meat or animal derived material (such as beef, chicken, turkey, lamb, fish, blood plasma, marrow bone etc. or one or more thereof). The product alternatively may be meat free (preferably including a meat substitute such as soya, maize gluten or a soya product) in order to provide a protein source. The foodstuff may contain additional protein sources such as soya protein concentrate, milk proteins, gluten etc. The foodstuff may also contain a fat source such as one or more of chicken fat, turkey fat, beef fat, duck fat, pork fat, lamb fat, etc., fish oil, sunflower oil, vegetable oil, etc. The foodstuff may also contain a starch source such as one or more grains (e.g. wheat, corn, rice, oats, barley etc.), or may be starch free.

The pet foodstuff preferably has a low caloric density. Caloric density (or energy density) of a food is a measurement of the average calories per weight (gram or ounce) of that food. Foods that are low in caloric density tend to be high in water and low in fat. The foodstuff may also comprise bulking agents, such as non-digestible fibre or carbohydrate to provide the caloric density required.

The foodstuff may be used alone or may be used in combination with a complete and balanced food which provides all the recommended vitamins and minerals for the companion animal in question, for example, as described in National Research Council, 2006, Nutrient Requirements for Dogs and Cats, National Academy Press, Washington D.C. (ISBN:0-309-08628-0); or Association of American Feed Control Officials, Official Publication 2015.

The present description includes a method for preparing the pet foodstuffs as described herein. The process for the manufacture of the foodstuff as described herein can be made according to any method known in the art.

The remaining components of the foodstuff are not essential to the invention and typical standard products can be included. The combined ingredients of the foodstuff according to the invention can provide all of the recommended vitamins and minerals for the particular animal in question (a complete and balanced food).

The pet foodstuff may include one or more nutrients selected from group (a) and group (b), wherein the nutrients in group (a) are aspartic acid, serine, glutamic acid, glycine, alanine or proline and the nutrients in group (b) are myristic acid, palmitic acid, stearic acid, palmitoleic acid, oleic acid or linolenic acid.

For example, the table below sets out the two sets of nutrient groups, as described:

| Group A | Group B |
| --- | --- |
| Aspartic Acid | Myristic Acid |
| Serine | Palmitic Acid |
| Glutamic Acid | Stearic Acid |
| Glycine | Palmitoleic Acid |
| Alanine | Oleic Acid |
| Proline | Linolenic Acid |

The pet foodstuff may be any combination of nutrients from group (a) and group (b). The pet foodstuff may comprise aspartic acid, serine, glutamic acid, glycine, alanine or proline or any combination thereof and myristic acid, palmitic acid, stearic acid, palmitoleic acid, oleic acid or linolenic acid or any combination thereof.

The pet foodstuff may include one nutrient from group (a) (i.e. are aspartic acid, serine, glutamic acid, glycine, alanine or proline) and one nutrient from group (b) (i.e. myristic acid, palmitic acid, stearic acid, palmitoleic acid, oleic acid or linolenic acid). In particular, when the pet foodstuff comprises one nutrient from each of group (a) and (b), the nutrients can be provided in a ratio of the group (a) nutrient to the Group (b) nutrient of 1:0.006 to 1:4.5 on a gram:gram as fed or dry matter basis.

The pet foodstuff may include two nutrients from group (a) (i.e. are aspartic acid, serine, glutamic acid, glycine, alanine or proline) and two nutrients from group (b) (i.e. myristic acid, palmitic acid, stearic acid, palmitoleic acid, oleic acid or linolenic acid). In particular, when the pet foodstuff comprises two nutrient from each of group (a) and (b), the nutrients can be provided in a ratio of the group (a) nutrient to the Group (b) nutrient of 1:0.014 to 1:3.5 on a gram:gram as fed or dry matter basis.

The pet foodstuff may include three nutrients from group (a) (i.e. are aspartic acid, serine, glutamic acid, glycine, alanine or proline) and three nutrients from group (b) (i.e. myristic acid, palmitic acid, stearic acid, palmitoleic acid, oleic acid or linolenic acid). In particular, when the pet foodstuff comprises one nutrient from each of group (a) and (b), the nutrients can be provided in a ratio of the group (a) nutrient to the Group (b) nutrient of 1:0.025 to 1:2.5 on a gram:gram as fed or dry matter basis.

Blood samples are taken from the companion animal, at least once before a meal and one or more times after the meal. In particular, the blood samples can be taken one or more times after the meal at chosen intervals between at least 30 minutes to 5 hours after the meal (for example: every 15 minutes, every 30 minutes, every hour or at 15 minutes, 60 minutes, 120 minutes and 300 minutes following the end of the 20 minute meal). The meal referred herein is the pet food stuff described having the particular protein to fat levels. Each blood sample taken from the companion animal is tested using standard assays, known in the art, to determine the concentration levels of biomarkers, for example 3-methylhistidine. The timed intervals at which the samples are taken and the GIP concentrations measured are not to be strictly timed and are approximate in time.

The concentration levels of 3-methylhistidine in the blood sample post prandially (i.e. after the companion animal has been fed the meal comprising the particular protein to fat ratio as described herein) are reduced when compared with the measurement of 3-methylhistidine taken when the companion animal is fed a meal not having the particular protein to fat ratio as described herein. In particular, the concentrations of 3-methylhistidine are significantly reduced when compared to the measurements of 3-methylhistidine taken when the companion animal is fed the foodstuff having other protein to fat ratios other than that described herein.

Feeding a companion animal, in particular a cat, a pet foodstuff having the particular protein to fat ratio as described herein, reduces the post-prandial levels of 3-methylhistidine significantly and thus provide the companion animal with beneficial health effects such as preventing and/or reducing sarcopenia, for example muscle breakdown and wastage in the companion animal.

The method can include the step of preparing the pet foodstuffs used in the present invention. The process for the manufacture of the foodstuff used in the present invention can be made according to any method known in the art.

The method of the invention as described can also include a step of formulating the foodstuff comprising a protein to fat ratio of 1:0.27 to 1:0.63 on a gram:gram as fed or dry matter basis (as described herein) which occurs prior to the step of feeding the cat the foodstuff.

The pet foodstuff can be also be used in the form of a dietary regime, wherein the dietary regime comprises a wet foodstuff and dry foodstuff that enables the companion animal to achieve the particular protein:fat ratio as described herein through the consumption of both the wet and dry foodstuffs. Each of the wet and dry foodstuffs have a protein:fat ratio within the range 1:0.27 to 1:0.63 on a gram:gram as fed or dry matter basis.

The foodstuffs may be provided at the same time, to enable the animal to eat both types of foodstuff at the same meal to achieve the particular protein to fat ratio as described herein through the consumption of both the wet and dry foodstuffs. Alternatively, the wet food, for example, may be provided in the morning and the dry foodstuff may be provided as a separate meal in the afternoon or evening, meaning that in the course of 24 hours, the animal will achieve the particular protein:fat ratio as described.

With the foods provided in this dietary regime, the preferred protein:fat ratio of the invention (1:0.27 to 1:0.63 gram:gram as fed or dry matter basis) may be achieved by the companion animal self-selecting the required amounts of each of the wet and/or dry foodstuffs provided to it. The preferred protein:fat ratio may be achieved by the consumption of the only the wet food or only the dry food or through a combination of each of the wet and the dry foodstuff provided to the companion animal.

The levels of 3-methylhistidine can be measured at the beginning of the day, prior to the companion animal being fed and post-prandially after the first meal of the day to obtain one measurement and then again prior to the companion animal being fed the second meal of the day and post-prandially after the second meal of the deal to obtain a second reading. Each of the wet and dry foodstuffs have a protein:fat ratio within the range 1:0.27 to 1:0.63 on a gram:gram as fed or dry matter basis, so the levels of 3-methylhistidine will have decreased post-prandially after both the first and second meal.

The invention also provides a kit comprising a first package comprising a wet foodstuff and second package comprising a dry foodstuff for use in such a dietary regime. Each of the wet and dry foodstuffs have a protein:fat ratio within the range 1:0.27 to 1:0.63 on a gram:gram as fed or dry matter basis and/or below or above the range 1:0.27 to 1:0.63 on a gram:gram as fed or dry matter basis and wherein when combined provide the protein:fat ratio within the range 1:0.27 to 1:0.63 on a gram:gram as fed or dry matter basis.

The invention further provides a kit comprising a first stage pet foodstuff and a second stage pet food stuff, and a package for separately housing the first stage pet foodstuff and the second stage pet foodstuff, wherein the first stage pet foodstuff comprises a ratio of protein:fat of 1:0.27 to 1:0.63 on a gram:gram as fed or dry matter basis and has a first caloric density, and wherein the second stage pet foodstuff comprises a ratio of protein:fat of 1:0.27 to 1:0.63 on a gram:gram as fed or dry matter basis and has a second caloric density, wherein the second caloric density is less than the first caloric density and wherein the first stage pet foodstuff is for feeding to a cat from the age of 1 to approximately 8 years of age and wherein the second stage pet foodstuff is for feeding to a cat above 8 years of age, for use in reducing and/or preventing sarcopenia.

The foodstuff may also comprise bulking agents, such as non-digestible fibre or carbohydrate to comprise the caloric density required.

The first caloric density of the first stage pet foodstuff is high, in that it contains more calories per weight of the food (i.e. more calories per gram of food), for example may contain more carbohydrate and more fat.

The second caloric density of the second stage pet foodstuff is low, in that it contains less or low amount of calories per weight of the food (i.e. less or low amount of calories per gram of food), for example may contain more water or be low in fat.

The kit as described may further comprise an insert placed in the second stage pet foodstuff compartment including feeding instructions. For example, instructions to switch the feeding of the first stage foodstuff to the second stage foodstuff once the companion animal reaches approximately 8 years of age (i.e. senior).

The invention also provides a kit comprising a pet foodstuff comprising a ratio of protein:fat of 1:0.27 to 1:0.63 on a gram:gram as fed or dry matter basis and has a high caloric density (i.e. a first stage pet foodstuff) and instructions for feeding the cat from the age of approximately 8 a pet foodstuff comprising a ratio of protein:fat of 1:0.27 to 1:0.63 on a gram:gram as fed or dry matter basis and having a low caloric density.

The foodstuff as described is fed to a companion animal, in particular a senior companion animal (for example a senior cat aged 8 years and/or above). It has been shown that feeding the pet foodstuff as described to a companion animal, in particular to a cat, results in post-prandial levels of 3-methylhistidine that are significantly maintained and/or reduced.

The invention also relates to a method of preventing and/or reducing sarcopenia in a companion animal, wherein the companion animal is fed (administered) a pet foodstuff comprising the particular ratio of protein:fat of 1:0.27 to 1:0.63 on a gram:gram as fed or dry matter basis.

Preferred features of the invention apply mutatis mutandis.

EXAMPLES

The invention will now be further described by way of reference to the following Example and FIGURE, which are provided for the purpose of illustration only and are not to be construed as being limiting on the invention.

Fold change is a measure describing how much a quantity changes going from an initial to a final value. For example, an initial value of 30 and a final value of 60 corresponds to a fold change of 1 (or equivalently, a change to 2 times), or in common terms, a one-fold increase.

Aim of the study was to determine different benefits from macronutrient diets in cats and to investigate the difference in macronutrient compositions on post-prandial metabolite profiles in cats.

A study was performed in 19 cats aged between 1 and 2 years to investigate the impact of 5 diets on various aspects of metabolism. Five diets (labelled Diet 1, Diet 2, Diet 3, Diet 4, and Diet 5) were manufactured using the same raw materials but in different proportions to provide a range of protein to fat ratios.

All cats were fed in five consecutive phases of 14 days in a randomised crossover design with each cat being fed each of the 5 diets in turn. All cats were within 5% of ideal body weight at the start of the trial. For the first 13 days of each phase, cats were fed two meals per day in amounts to maintain a stable, healthy bodyweight. On day 14 of each phase, cats had blood samples taken at 5 time points (one prior to feeding as a baseline and then at 15, 60, 120, & 300 mins following the end of the 20 minute meal).

TABLE 1

Diet compositions and ratio of Protein:Fat

| Diet | Protein g/100 g | Carbohydrate g/100 g | Fat g/100 g | Energy kcal/100 g | P:F |
|---|---|---|---|---|---|
| 1 | 7.87 (low) | 2.55 (low) | 11.47 (high) | 132 | 1:1.46 |
| 2 | 7.47 (low) | 9.93 (medium) | 7.67 (medium) | 125 | 1:1.03 |
| 3 | 7.00 (low) | 12.68 (high) | 5.30 (medium) | 119 | 1:0.76 |
| 4 | 10.90 (high) | 2.71 (low) | 4.00 (medium) | 95 | 1:0.37 |
| 5 | 11.60 (high) | 9.87 (high) | 1.30 (low) | 92 | 1:0.11 |

TABLE 2

Concentrations of certain amino acids and fatty acids present in the diet associated with the beneficial effects (diet 4).

| Nutrient | Concentration in diet (g/100 g as fed) |
|---|---|
| Aspartic Acid | 0.74 |
| Serine | 0.38 |
| Glutamic Acid | 1.14 |
| Glycine | 0.9 |
| Alanine | 0.6 |
| Proline | 0.55 |
| Myristic Acid | 0.03 |
| Palmitic Acid | 0.58 |
| Stearic Acid | 0.25 |
| Palmitoleic Acid | 0.13 |
| Oleic Acid | 0.90 |
| Linolenic Acid | 0.04 |

Two types of mass spectrometry analyses were applied to all samples. GC-MS (gas chromatography-mass spectrometry; Agilent 6890 GC coupled to an Agilent 5973 MS-System, Agilent, Waldbronn, Germany) and LC-MS/MS (liquid chromatography-MS/MS; Agilent 1100 HPLC-System (Agilent, Waldbronn, Germany) coupled to an Applied Biosystems API4000 MS/MS-System (Applied Biosystems, Darmstadt, Germany)) were used for broad profiling (van Ravenzwaay et al. 2007).

Proteins were removed from plasma samples (60 µl) by precipitation. Subsequently polar and non-polar fractions were separated for both GC-MS and LC-MS/MS analysis by adding water and a mixture of ethanol and dichloromethane. For GC-MS analyses, the non-polar fraction was treated with methanol under acidic conditions to yield the fatty acid methyl esters derived from both free fatty acids and hydrolyzed complex lipids. The polar and non-polar fractions were further derivatized with O-methyl-hydroxyamine hydrochloride (20 mg/ml in pyridine, 50 µl) to convert oxo-groups to O-methyloximes and subsequently with a silylating agent (MSTFA, 50 µl) before GC-MS analysis. For LC-MS/MS analyses, both fractions were reconstituted in appropriate solvent mixtures. High performance LC (HPLC) was performed by gradient elution using methanol/water/formic acid on reversed phase separation columns. Mass spectrometric detection technology was applied as described in the U.S. Pat. No. 7,196,323, which allows targeted and high sensitivity "Multiple Reaction Monitoring" profiling in parallel to a full screen analysis. To account for inter- and intra-instrumental variation in both GC-MS and LC-MS/MS profiling, data were normalised to the median of reference samples derived from a pool formed from aliquots of all samples from that species. Pooled reference samples were run in parallel through the whole process. The limit of detection and the dynamic range of the semi-quantitative measurements were determined by dilution and spiking experiments during method development. Daily, the signal-to-noise (S/N) ratio threshold of 15 was used for a metabolite to be considered "semi-quantitative".

Data Analysis

Data analysis included univariate statistics (mixed linear models) and multivariate analyses (principal component analysis (PCA)).

Multivariate Statistics

All metabolite data were log-transformed (to ensure an approximate normal distribution), centered and scaled to unit variance. Multivariate analysis was performed using the software Simca (version 13; Umetrics AB, Umeå, Sweden).

Univariate Statistics

For the entire dataset and each individual group to be analyzed statistically, the minimum, maximum, mean and median values were determined. Mean and median values were calculated on a logarithmic scale and then back-transformed to non-logarithmic scale.

Figures were constructed in JMP with 95% Confidence Intervals.

Results

The study surprisingly showed that cats fed diets with protein to fat ratios of 1:0.37 (diet 4) had low fasting levels of 3-methylhistidine (a marker of muscle breakdown) which did not increase following food intake. In contrast, consumption of other diets with different protein:fat ratios resulted in either increased fasting levels of 3-methylhistidine, increased post-prandial levels of 3 methylhistidine or both. A low level of 3-methylhistidine is indicative of minimal muscle breakdown whereas increased levels of 3-methylhistidine are consistent with increased breakdown of muscle protein.

The results therefore show that the ratio of protein to fat in the food can have a marked impact on the breakdown of muscle protein in the cat. Based on these results, diets with a protein to fat ratio the same as diet 4 (i.e. 1:0.37) and within a range either side of that of diet 4 (i.e. 1:0.27 to 1:0.63) would provide a benefit to the cat of reducing muscle breakdown in comparison to the other diets and therefore can lead to minimising muscle turnover and may lead to better metabolic responses to perturbation, healthier longevity and improved outcome with ageing.

Figure 1:
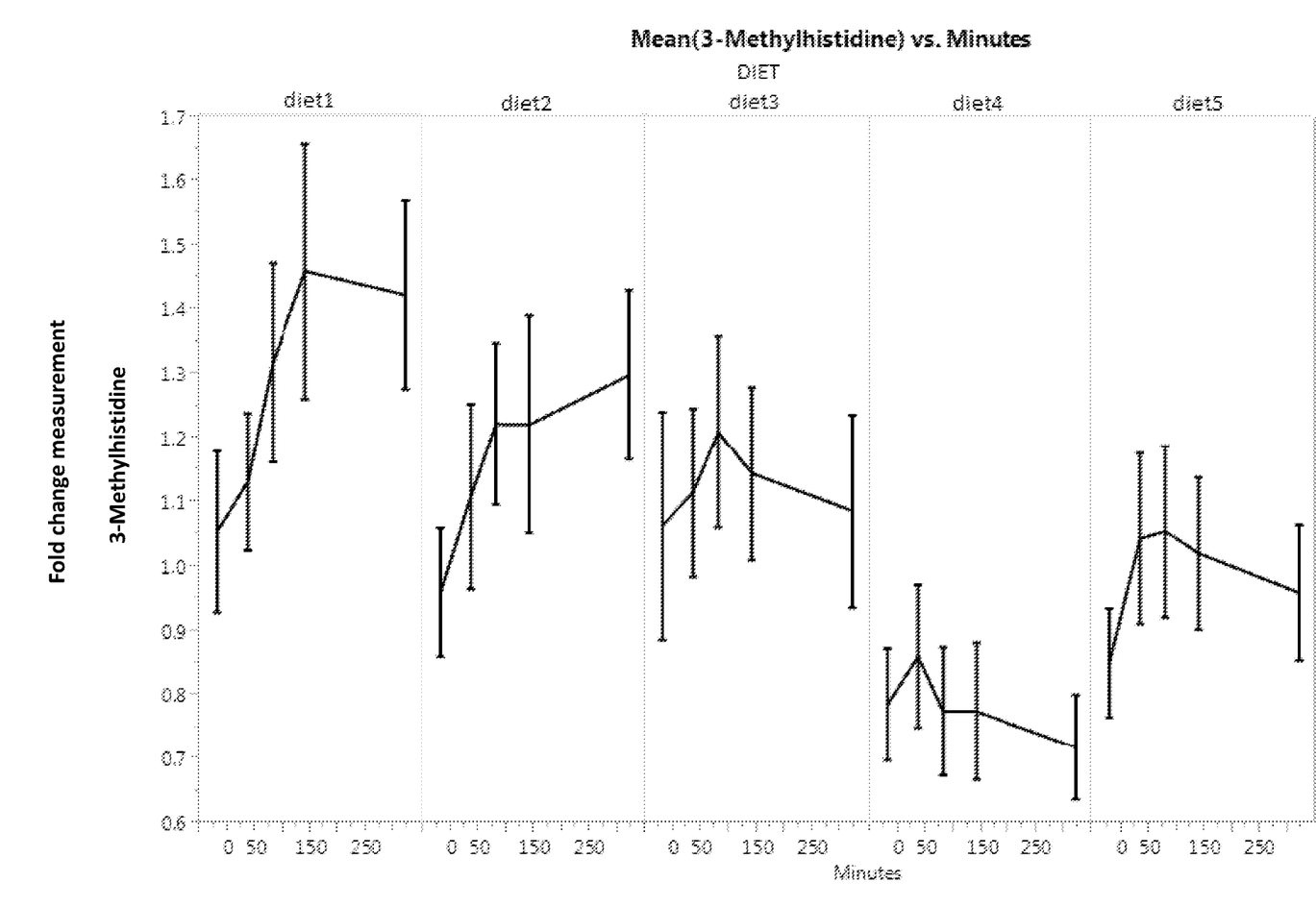
FIG. 1: Graph showing plasma levels of 3-methylhistidine in cats fed the diets over time. The graph shows that cats fed Diet 4 (having P:F of 1:0.37 gram:gram as fed or dry matter basis) obtained low and stable plasma levels of the muscle breakdown product 3-methylhistidine compared to the other diets. The y axis is a fold change measurement.

At all sample points after meals of Diets 1, 2, 3 and 5, the 3-methylhistidine concentrations were significantly higher than after Diet 4. From 30 minutes to an hour post meal until 325 minutes post meal, levels of GIP after Diets 1, 2, 3 and 5, were significantly higher than after Diet 4. (FIG. 1).

The benefits of reducing/preventing skeletal muscle breakdown by feeding a diet with a protein:fat ratio of 1:0.27 to 1:0.63 as described in the present invention are that normal skeletal muscle mass can be maintained for longer in the lifespan of the animal contributing to the avoidance of weakness, frailty and reduced activity commonly associated with aging in companion animals. Preventing/reducing skeletal muscle breakdown is also beneficial because an adequate skeletal muscle mass is essential to supply required amino acids in order to maintain the protein turnover of vital tissues and organs in the post-absorptive state and potentially to provide substrate for gluconeogenesis in both fed and fasted states.

The invention claimed is:

1. A method comprising:
   (a) measuring a level of 3-methylhistidine in a blood sample from a cat,
   (b) feeding a cat a foodstuff comprising a protein to fat ratio of 1:0.27 to 1:0.63 on a gram:gram as fed or dry matter basis, and further comprising i) one or more of aspartic acid, serine, glutamic acid, glycine, alanine and proline, and ii) one or more of myristic acid, palmitic acid, stearic acid, palmitoleic acid, oleic acid, and linolenic acid, wherein the ratio of i) to ii) is 1:0.006 to 1:4.5 on a gram:gram as fed or dry matter basis, and
   (c) measuring the level of 3-methylhistidine in a blood sample from the cat after feeding the foodstuff, wherein a reduction and/or maintenance in 3-methylhistidine level post-prandially is indicative of a foodstuff effective at reducing skeletal muscle breakdown in a cat.

2. The method of claim 1, wherein the cat is above 8 years of age.

3. The method of claim 1, wherein the levels of 3-methylhistidine are measured at least once between an hour or immediately before the foodstuff is fed to the cat and at least once between at least 30 minutes to 5 hours after the foodstuff has been fed to the cat.

4. The method of claim 1, wherein the foodstuff has a protein to fat ratio of about 1:0.33 to 1:0.55 on a gram:gram as fed or dry matter basis.

5. The method of claim 1, wherein the foodstuff has a protein to fat ratio of about 1:0.45 on a gram:gram as fed or dry matter basis.

6. The method of claim 1, wherein the foodstuff has a protein to fat ratio of about 1:0.37 on a gram:gram as fed or dry matter basis.

7. The method of claim 1, wherein the foodstuff is a nutritionally balanced pet foodstuff.

8. The method of claim 1, wherein the foodstuff has a low caloric density.

9. The method of claim 1, further comprising a step of formulating a foodstuff comprising a protein to fat ratio of 1:0.27 to 1:0.63 on a gram:gram as fed or dry matter basis prior to feeding the cat the foodstuff.

* * * * *